(12) United States Patent
Wilcox

(10) Patent No.: US 6,364,849 B1
(45) Date of Patent: Apr. 2, 2002

(54) SOFT TISSUE DIAGNOSTIC APPARATUS AND METHOD

(75) Inventor: Ariel Wilcox, Dixmont, ME (US)

(73) Assignee: Access Wellness and Physical Therapy, Bangor, ME (US)

( * ) Notice: Subject to any disclaimer, the term of this patent is extended or adjusted under 35 U.S.C. 154(b) by 0 days.

(21) Appl. No.: 09/562,964

(22) Filed: May 3, 2000

Related U.S. Application Data

(60) Provisional application No. 60/132,169, filed on May 3, 1999.

(51) Int. Cl.[7] .............................................. A61B 5/103
(52) U.S. Cl. ..................... 600/587; 600/437; 600/443
(58) Field of Search .......................................... 600/449

(56) References Cited

U.S. PATENT DOCUMENTS

| | | | |
|---|---|---|---|
| 4,216,766 A | 8/1980 | Duykers et al. | |
| 4,390,026 A | 6/1983 | Christman | |
| 4,501,151 A | 2/1985 | Christman | |
| 4,509,524 A | 4/1985 | Miwa | |
| 4,819,621 A | 4/1989 | Ueberle et al. | |
| 4,947,851 A | 8/1990 | Sarvazyan et al. | |
| 5,058,591 A | * 10/1991 | Companion et al. | 600/449 |
| 5,115,808 A | 5/1992 | Popovic et al. | |
| 5,388,583 A | 2/1995 | Ragauskas et al. | |
| 5,458,130 A | 10/1995 | Kaufman et al. | |
| 5,545,124 A | 8/1996 | Krause et al. | |
| 5,561,371 A | 10/1996 | Schenck | |
| 5,615,681 A | 4/1997 | Ohtomo | |
| 5,713,356 A | 2/1998 | Kruger | |
| 5,749,364 A | 5/1998 | Sliwa, Jr. et al. | |
| 5,795,311 A | 8/1998 | Wess | |
| 5,817,018 A | 10/1998 | Ohtomo | |
| 5,829,439 A | 11/1998 | Yokosawa et al. | |
| 5,833,603 A | 11/1998 | Kovacs et al. | |

* cited by examiner

*Primary Examiner*—John P. Lacyk
*Assistant Examiner*—Pamela Wingood
(74) *Attorney, Agent, or Firm*—Marc S. Kaufman; Nixon Peabody LLP

(57) ABSTRACT

A soft tissue diagnostic apparatus for diagnosis of stress and injury in anatomical soft tissue by detecting the response of the soft tissue to acoustic energy and a method of detecting soft tissue damage or stress and treating the tissue. An acoustic transmitter transmits excitation acoustic energy toward a target area of soft tissue of a subject. An acoustic receiver receives responsive acoustic energy generated by the soft tissue in response to the excitation acoustic energy transmitted by the acoustic transmitter and generates an output signal representative of the response of the soft tissue to the excitation acoustic energy. An analyzer receives the output signal of the acoustic receiver and provides an indication of at least one of stress and injury in the soft tissue based on the output signal.

9 Claims, 9 Drawing Sheets

SOFT TISSUE DIAGNOSTIC APPARATUS AND METHOD

RELATED APPLICATION DATA

This application claims benefit of Provisional Application Serial No. 60/132,169 filed on May 3, 1999, the disclosure of which is incorporated herein by reference.

BACKGROUND OF THE INVENTION

1. Field of the Invention

The invention relates to diagnosis of the source of soft tissue pain. More particularly, the invention is a method and apparatus for measuring responses of soft tissue subject to acoustic stimulation, processing the response, and interpreting the response to indicate the location of stress and/or injury in soft tissue; and for verifying the effectiveness of treatment of soft tissue.

2. Description of the Related Art

Existing techniques for diagnosis of the source of pain in soft tissue are relatively subjective and inaccurate. Typically, clinicians rely upon responses to patient questionnaires, medical histories, and subjective observation to diagnose the source of pain in soft tissue. These tools are inherently imprecise even when used in a meticulous manner. Several expensive technologies have been applied to diagnosis of the source of soft tissue pain. For example, magnetic resonance imaging (MRI), x-rays, and computerized tomography (CT) are known noninvasive technologies. Invasive technologies include nerve blocks, probes, and the like. Even when utilizing these technologies, results are frequently inaccurate or inconclusive. Multiple studies have shown that x-rays have little value in routine examination of the source of soft tissue pain. Even MRI is now only rarely recommended in back pain, since surgery based on such imaging has had a high failure rate. Moreover, the demonstration of abnormal scans and x-rays in people who lack back pain symptoms casts serious doubt upon the value of these technologies in soft tissue diagnosis.

Other diagnostics have little value in diagnosing the source of soft tissue pain. Nerve conduction studies and electromyography are indicated for detection of nerve damage only at advanced stages. Measurement devices for indicators of tissue mobility or tension are limited in scope and applicability. Ultrasound may image large muscle tears and can depict certain tissue, but not specifically pain or stress in tissue. Nerve blocks may identify an area of pain but are not suited for routine evaluation because skilled administration of injected anesthetic agents are required and risk factors are elevated. Blood flow analyses also have limited relevance to soft tissue pain.

Serum and saliva analyses for substances associated with pain have been used to diagnose the source of pain. However, protocols, norms, and standardization of sampling and processing techniques have yet to be established for such analyses. One theory is that visualization of chronic neck-shoulder pain can be achieved through the quantification of lowered microcirculation. However, this quantification requires the insertion of optical laser-Doppler single-fibers into two muscle sites concurrently with increased static contraction using electromyography. Of course, this method, even if proven to be accurate, is painful and has a high risk factor.

It is known to use acoustic energy to determine physical properties of various nonliving materials. Also, acoustic energy has been used in various medical applications. For example, U.S. Pat. No. 5,795,311 discloses an apparatus for treating tissue by imparting acoustic energy thereto. U.S. Pat. No. 5,458,130 discloses an apparatus which applies ultrasonic energy for measuring bone density, and strength, and for treating musculoskeletal tissue using a complex signal generator and processing system. U.S. Pat. No. 4,509,524 discloses a device for characterizing tissue based on reflected ultrasonic waves. U.S. Pat. No. 4,819,621 discloses an apparatus for detecting cavitation in tissue injuries by detection of a reflected acoustic signal. U.S. Pat. No. 4,216,766 discloses an apparatus for treating tissue by applying acoustic energy at the resonant frequency of a gas filled cavity surrounding the tissue to be treated. U.S. Pat. No. 5,115,808 discloses an apparatus for measuring the velocity of acoustic signals in tissue for determining the shear elastic properties of the tissue. U.S. Pat. No. 5,545,124 discloses a method for alleviating pain by charging tissue with acoustic shockwaves. However, the prior art does not permit reliable detection of stress in soft tissue through noninvasive measures. Accordingly, the prior art fails to provide a method or apparatus for diagnosing the source of pain due to soft tissue damage or stress.

Therefore, a vast area of difficult and often intractable syndromes of pain defy quantification and thus are difficult to treat in a reliable manner. Conventional diagnostic investigation often yields limited or equivocal findings, and involves expensive, painful and indirect methods. It follows that, therapeutic measures are compromised by this lack of resources.

The phrase "soft tissue" as used herein includes muscles, ligaments, connective tissue and fascia, nerve and blood vessel walls, and other essential structures of the body. Diagnostic designations relating to these tissues include chronic pain, strain, musculoskeletal pain and injury, myofascial pain and injury, benign, non-malignant, or idiopathic pain; myalgia, fibrositis, or fibromylalgia; repetitive strain injury (RSI) or overuse injury, including carpal tunnel syndrome (CTS), epicondylitis, tennis elbow, bursitis and tendinitis, temporomandibular joint disorder (TMD or TMJ), orofacial and neck pain, several types of headache, pelvic pain of unknown etiology, and back pain (all of which are included in the classification of "soft tissue pain" as used herein). The onset of soft tissue pain may have had an identifiable traumatic component, but the duration of the pain often far exceeds the expected physiological process of recovery. Gross damage and disease processes are often absent with soft tissue pain.

The economic impact of soft tissue pain is reported by such studies as those of the annual combined cost of back pain-related medical care and disability compensation, which alone may reach $50 billion annually in the U.S. Back pain affects about 31 million Americans, is the leading cause of activity limitation in young adults, and generates annual U.S. productivity losses in the range of $28 billion. Incidence of tension-type headaches has been reported as high as 48.9%, with numerous annual lost workdays and days of decreased effectiveness at work, home, or school. Neck pain occurred at a 34% rate in one study. These statistics are representative of the magnitude of the of soft tissue pain which is severely hampered by lack of efficient diagnosis. It is frequently difficult to differentiate between specific conditions which benefit from surgery and those which do not. Despite due care in evaluation, surgery fails a significant percentage of patients who do not obtain relief and whose condition may even worsen. Conversely, surgical interventions performed for non-pain reasons are themselves a recognized cause of chronic soft tissue pain which is difficult to identify.

SUMMARY OF THE INVENTION

It is an object of the invention to permit abnormalities, such as stress and damage of soft tissue to be detected in a non-invasive manner.

It is another object of the invention to facilitate diagnosis of soft tissue pain.

It is another object of the invention to facilitate treatment of soft tissue pain.

It is another object of the invention to locate areas of abnormalities, such as soft tissue stress and damage, in an objective manner.

It is another object of the invention to confirm the effectiveness of treatment of soft tissue injury.

To achieve these objects, a first aspect of the invention is a soft tissue diagnostic apparatus for diagnosis of stress and injury in anatomical soft tissue by detecting the response of the soft tissue to acoustic energy. The apparatus comprises an acoustic transmitter configured to transmit excitation acoustic energy toward a target area of soft tissue of a subject, an acoustic receiver configured to receive responsive acoustic energy generated by the soft tissue in response to the excitation acoustic energy transmitted by the acoustic transmitter and generating an output signal representative of the response of the soft tissue to the excitation acoustic energy, and an analyzer coupled to the acoustic receiver to receive the output signal of the acoustic receiver, to process the signal, and to provide an indication of at least one of stress and injury in the soft tissue based on the output signal.

BRIEF DESCRIPTION OF THE DRAWING

The invention will be described through a preferred embodiment and the attached drawing in which.

DETAILED DESCRIPTION OF THE PREFERRED EMBODIMENT

Figure 1:
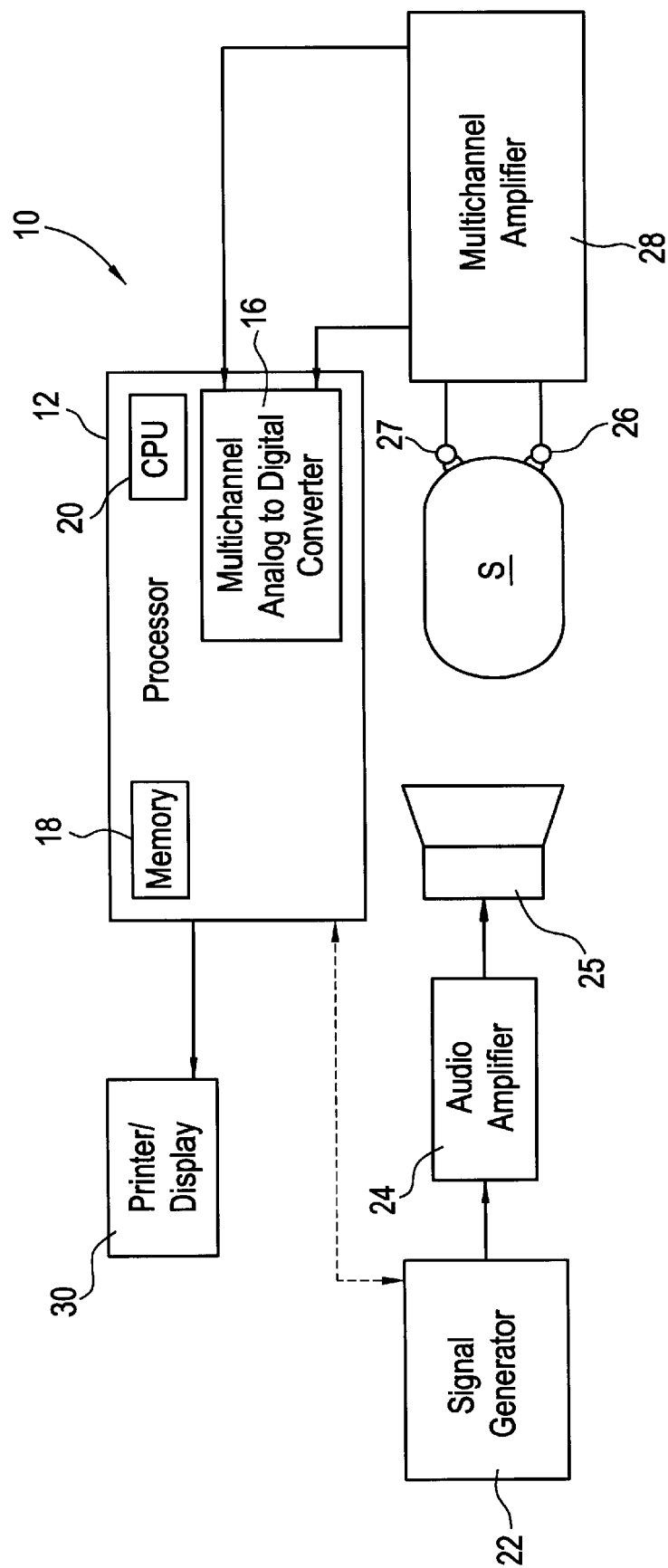
FIG. 1 is a block diagram of a test apparatus for verifying the underlying principles of the preferred embodiment.

Scientific research has identified a model called "tensegrity" which provides form, flexibility, communication, response, strength and resilience throughout the body's structure. The tensegrity structural components of the body, from DNA and cytoskeleton to entire cells and tissues, exhibit characteristic resonant frequencies of vibration. Studies have shown that the matrix of tensegrity maintains a force balance which provides a means to integrate mechanics and biochemistry at the molecular level. Physical forces are converted into biological responses when mechanically induced information is transmitted through the molecular and cellular complexes. The tensegrity networks of the body mediate this mechanotransduction; their organizations have been found to function as coupled harmonic oscillators. Such mechanotransduction significantly influences cell function, tissue growth and remodeling, gene expression, and participates with ion channels, signaling molecules, proteins, lipids, chemical transmitters and more.

At the tissue level, ligaments, fascia, muscles, bones, and blood vessels demonstrate tensegrity structure and properties in their individual and intertwined organizations. These components constantly receive input and perform or adapt in response, demonstrating mechanical communication and information processing. The nervous system is another type of communication network involved with responses to internal or external stresses. In localized areas or centrally in the brain, neural tissue plays a large role in processing information, directing action and maintaining homeostasis. Neurally mediated responses such as voluntary movement, involuntary functions, and self protective reactions involve signal transfer processes. This communication is facilitated by the tensegrity structure on the cellular level and through nerve pathways as well as through tensegrity relationships between the musculoskeletal and other tissue participants.

The body's interactions with its internal and external environment involve a high level of complexity and coordination, yet the integrated network responds instantly. This is possible because the body is always in readiness at a level of internal tone called pre-stress, an isometric/elastic state which supports immediate mechanical responsiveness, in addition to essential balance, decompression, form and stability. Elevation of the normal pre-stress threshold interferes with the resiliency of the network. Translated to the soft tissues, excessive pre-stress causes restriction, stiffness, compression, and asymmetrical organization. Many cellular processes are altered or affected, including transmembrane receptors which participate in pain generation. Perpetuation and proliferation of these stresses result in tissue restriction and pathological adhesions, causing immobility and pain. Inflammatory responses may also be stimulated, producing pain signaling substances. Nerves may be irritated through traction or compression as well as biochemical transmission, providing yet another link between mechanical tensional dysfunctions and pain generation. Conduction of forces can lead to elevated stresses that are isolated or, more likely, networked into a domino effect, being recruited into patterns of reaction, reinforcement, and compensation. Dysfunction can proliferate throughout the tensegrity system. Therefore, diagnosis needs to be site-specific to the latent reaction that is perpetuating the strain and elevated pre-stress and it needs to be sensitive to the hierarchical compensatory and stabilizing strain relationships.

These relationships are organized into sites that applicant has termed "barriers" and "anchors". Barriers are areas of tissue reaction that exhibit tensional restriction of mobility when assessed through palpation and other techniques. Barriers are the result of irritation and strain patterns originating from stress reactions of the tissue at the anchor location. Anchors are the ultimate origin of the soft tissue injury and as such need to be precisely identified for accurate diagnosis of the injury etiology and effective treatment results. Anchors can be assessed through manual palpation techniques as follows: manual pressure and traction techniques on the anchor will produce temporary reduction of the tension at the barrier site as assessed by monitoring that site. Also, the entire length of the stress and strain reaction through the intervening tissues can be verified by applying pressure and traction at the anchor and barrier at each end which identifies the severe tissue immobility indicative of the injury. Accordingly, it is important, and difficult, to locate damaged or stressed soft tissue.

Strain that has exceeded the threshold of tolerance produces plastic changes involving residual tensional tone. In response to mechanical stresses, protective reactions of the nervous and soft tissue systems mobilize instantaneously, but do not resolve with the same efficacy. The excited nerve activity may persist, the pre-stress of the structural tensegrity may be re-set to an elevated level and the tensile quality of the tissue may become altered. Altered tensile quality results in altered acoustic response.

The relational barrier and anchor sites are characterized by certain acoustic responses. First, the acoustic response of the injury can be obtained at the barrier, the anchor, and in between along the length of the particular strain and tension involvement of the injury. This is a method for tracking the location of the strain reaction through the body. Second, when the anchor is stimulated acoustically the response can be determined at the barrier site, and in fact identifies its location; however, the reverse is not observed. This is a method for differentiation of the barrier and anchor by acoustic techniques. Third, the barrier is also identified by the larger amplitude of the characteristic acoustic response. Fourth, the anchor site location is also identified through tracking the characteristic acoustic response of the stressed tissue from the barrier to the point at which the response disappears.

Applicant has discovered that the alteration of density and tensile qualities of soft tissue due to stress changes the impedance and/or dispersion thereof, thus affecting acoustic properties thereof. The persistent state of elevated pre-stress that remains following excessive demand may significantly participate in the condition commonly identified as soft tissue injury. Thus, altered tensional dynamics of the soft tissue produce idiosyncratic acoustical responses which can be utilized as diagnostic indicators. Using signals preferably in the 100–1000 Hz frequency range with a population largely comprised of chronic pain patients, Applicant has noted localized palpable excitation in the area of injury, pain complaint, and/or tension. These sites have had a high correlation with nerve pathway location. Sensory nerve perception threshold measurements using a NEUROMETER™ have confirmed a concurrent functional impairment.

The invention quantifies acoustical responses of soft tissue to locate specific sites of tensional involvement and thus diagnose soft tissue stress or injury and to confirm the effectiveness of treatment thereof. Accordingly, the invention drastically reduces the level of skill required to locate and treat soft tissue injuries.

FIG. 1 is a block diagram of a test apparatus according to a preferred embodiment of the invention. Apparatus 10 includes processor 12 as an analyzer. In the preferred embodiment processor 12 is a microprocessor based digital device, such as a personal computer. However, any type of analyzer can be used, such as an analog signal processor, or the like. Processor 12 includes multichannel analog to digital converter A/D 16. Of course, if processor 12 is analog, A/D 16 can be omitted and replaced by appropriate analog signal interfaces. Processor 12 of the preferred embodiment also has memory device 18, which can include one or more of a random access memory (RAM), a magnetic disk memory device, an optical memory device, or the like, for storing instructions of a control program. Processor 12 also has central processing unit (CPU) 20 for executing the instructions of the control program. Display 30 is coupled to processor 12 to display test results, variables, and the like.

Signal generator 22 is configured to generate an electrical signal of predetermined frequency as described below. The operator can adjust the frequency of the electrical signal or select a progression of frequencies to be generated by signal generator 22 in a known manner. Amplifier 24 receives the electrical signal from signal generator 22 to drive speaker 25 serving as an audio source. The audio source can be any transducer capable of producing an acoustic vibrational signal in response to electrical impulses or other signals, such as a cone speaker, a planar driver speaker, or a piezoelectric device. Also, the signal provided to the audio source can be of any appropriate type. Signal generator 20, amplifier 24, and speaker 25 constitute an acoustic transmitter in the preferred embodiment. However, the acoustic transmitter can be any device for transmitting acoustic energy, such as a tuning fork, a tone generator, or the like. Preferably, the audio source is highly directional to be capable of isolating particular soft tissue areas.

Audio sensor 26 and audio sensor 27 are coupled to A/D 16 of processor 12 through multi channel amplifier 28. Audio sensors 26 and 27 and amplifier 28 constitute an acoustic receiver of the preferred embodiment. However, the acoustic receiver can be any device for receiving acoustic energy and distinguishing characteristics thereof, such as a selective resonator, the operator's ear, or the like. Sensors 26 and 27 can be microphones, styli, piezoelectric vibration sensors, optical motion sensors, accelerometers, or any other transducer capable of directly or indirectly sensing acoustic energy or motion and outputting a signal related thereto. Sensors 26 and 27 can be contact sensors or non-contact sensors. Processor 12 can include the necessary processing circuitry or software to eliminate background noise, such as 60Hz hum, to eliminate any undesired phase or amplitude of the received signal, or to otherwise, linearize, manipulate, transition or enhance the signals received from multichannel amplifier 28. For example, if microphones or any other non contact sensor are used as audio sensors 26 and 27, it may be necessary to filter out the phase of the audio signal generated by speaker 25 to avoid errors due to direct coupling between speaker 25 and audio sensors 26 and 27. Preferably, audio sensors 26 and 27 are directional to a high degree to minimize noise and environmental effects. Signal generator 22, amplifier 24 and amplifier 28 can be incorporated in processor 12. For example, a conventional sound card or interface can be used if processor 12 is a personal computer.

To use test apparatus 10 for diagnosis of soft tissue damage or stress, soft tissue S of a patient is placed proximate speaker 25 to be in the path of acoustic energy generated by speaker 25, as illustrated in FIG. 1. For example, the hand of the patient can be placed in front of speaker 25 if stress due to repetitive stress injury to the hand is to be located. Then, soft tissue S is stimulated with various frequencies of acoustic energy from speaker 25 to determine a frequency of maximum response amplitude as detected by sensors 26 and 27. The frequency of maximum response is used for further testing. For example, frequencies between 100 and 1000 Hz can be used at 70–90 db.

A barrier is then located using known techniques, such as palpation. Sensor 26 is placed on the barrier site and sensor 27 is placed on a control site at a soft tissue location that has normal tension determined through palpation. Sensors 26 and 27 are monitored while the tone is generated and the output signal thereof is recorded in memory 18 and processed as described below.

EXAMPLES

Applicant conducted tests using the apparatus of the preferred embodiment to confirm the effectiveness thereof and the repeatability of data acquired thereby. In the tests, barrier sites were located by a trained therapist using conventional techniques. However, barrier sites can be located using the apparatus of the preferred embodiment. Sensor 26 was placed in contact with skin over the tissue at the site of the barrier (i.e., a location of soft tissue tension and/or damage corresponding to an anatomical location of a nerve). Sensor 27 was placed in contact with skin at an adjacent normal (control) soft tissue location, near, but not connected to, the barrier. Signal generator 22 was actuated to cause acoustic energy in the range 100–1,000 Hz at amplitudes of approximately 70–90 db to be emitted from speaker 25 directed to the tissue. The frequency of the sound was varied to determine the maximum amplitude of response detected by sensors 26 and 27. The frequency of maximum amplitude was then used for further testing. In some tests, a tuning fork was used to generate acoustic energy instead of signal generator 22, amplifier 24, and speaker 25. In the latter case, the tuning fork was placed in contact with the body surface (e.g., in the case of lower back measurements, the tuning fork was placed on the skin above the spinal column near the sensors).

Figure 2:
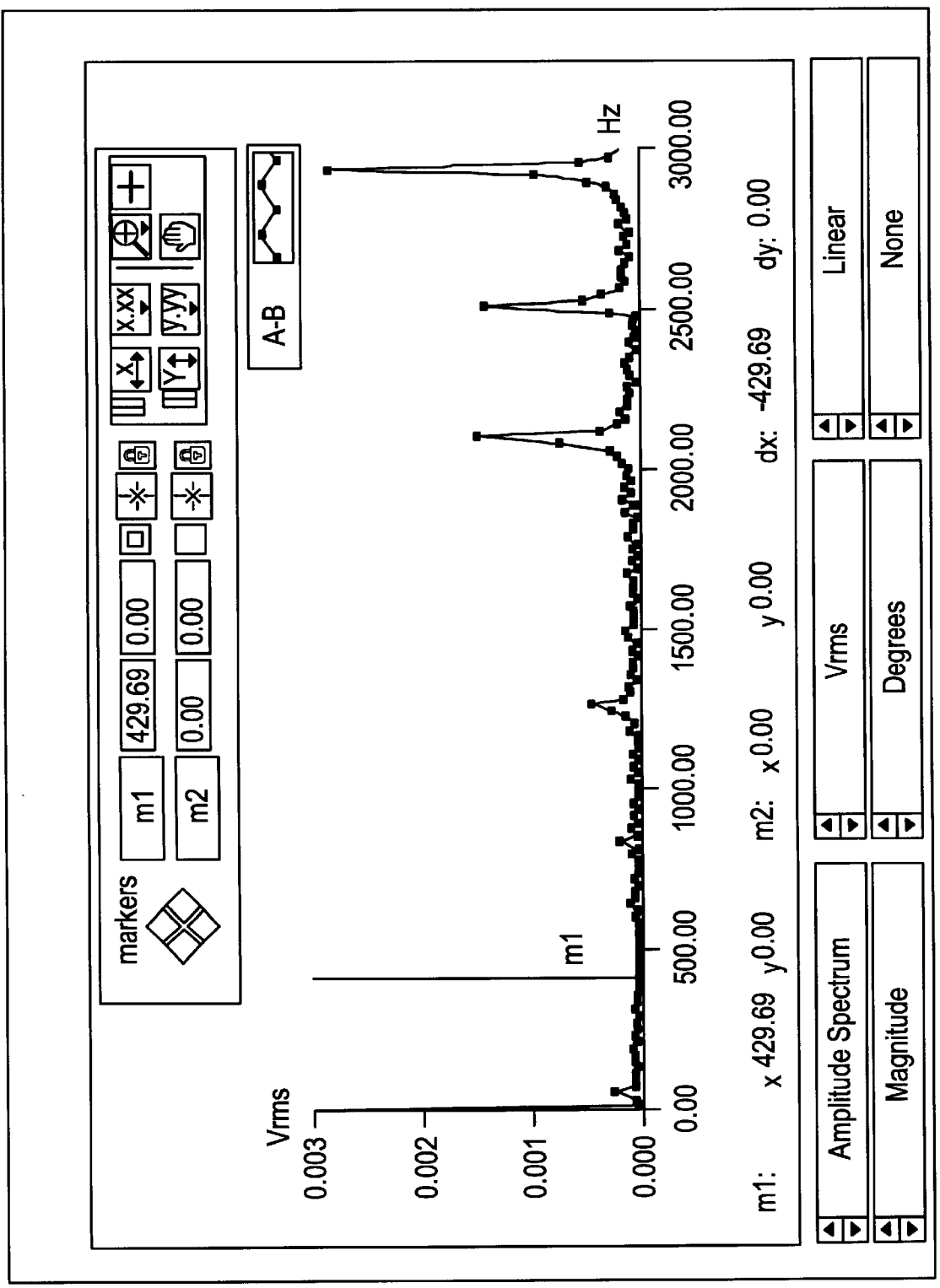
FIG. 2 is a graph of amplitude versus frequency of the transformed signal as a result of a first test of damaged tissue.

FIG. 2 illustrates the results of a first test conducted on a patient's back. Sensor 26 was placed on the skin above the injury barrier and sensor 27 was placed on a normal (i.e. non-injured) site near the barrier. Acoustic energy at a frequency of 430 hz was emitted through speaker 25 positioned about 6" above the tissue and equidistant from sensors 26 and 27. After the scaling, shifting, subtraction, and transformation processing described above, the results of FIG. 2 were observed. Note the spikes at frequencies above the fundamental frequency of 430 hz. In FIG. 2, spikes are observed at roughly 1300 hz, 2100 hz, and 2900 hz.

Figure 3:
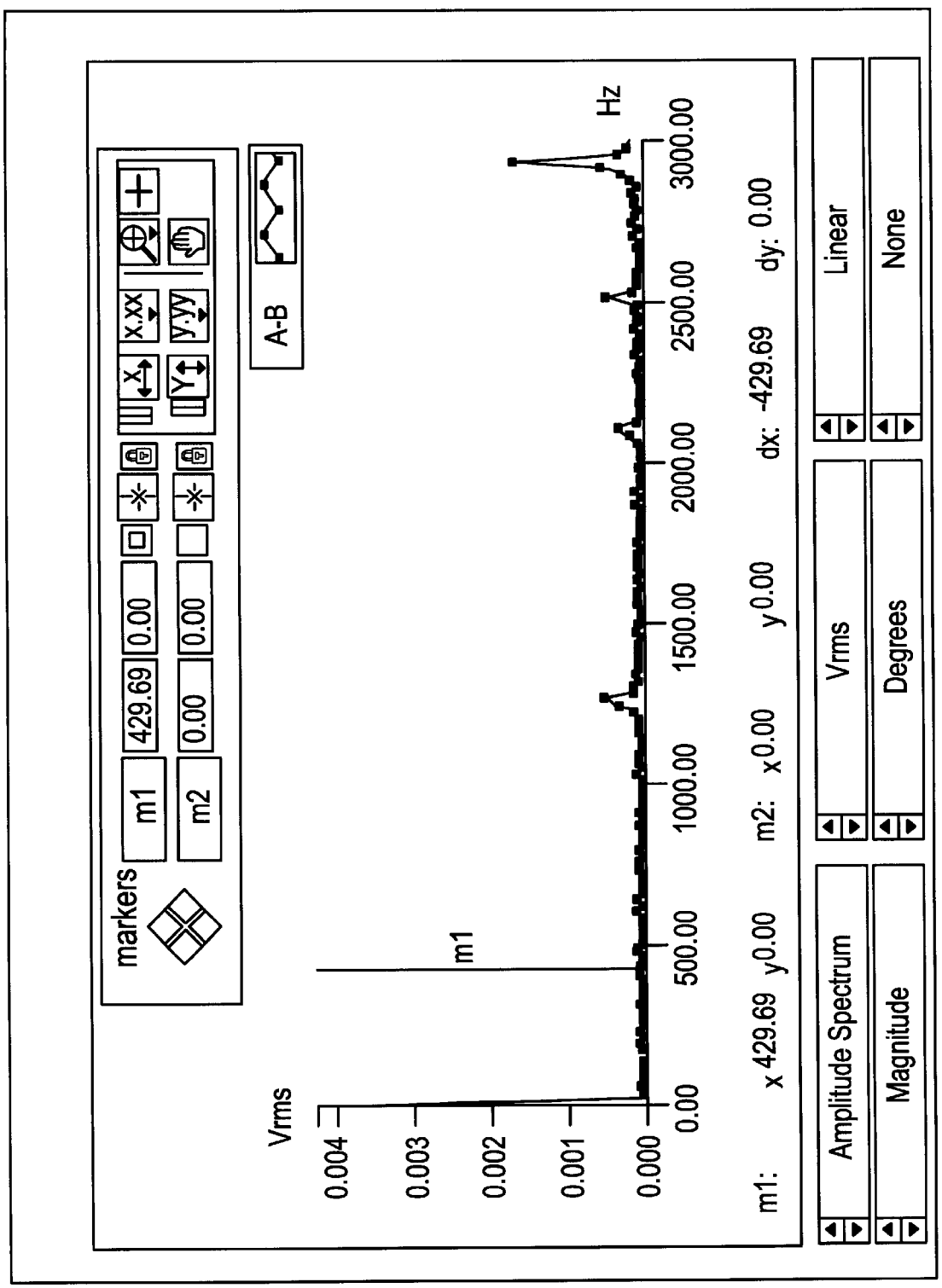
FIG. 3 is a graph similar to FIG. 2 for normal tissue.

Sensor 26 was then removed from the barrier location and relocated to be over a normal (i.e. non-injured) tissue portion on the same patient. After otherwise identical data collection and processing, the results of FIG. 3 were obtained. It is apparent that the spikes at frequencies above the fundamental frequency are substantially attenuated when both sensors are placed over normal tissue.

Figure 4:
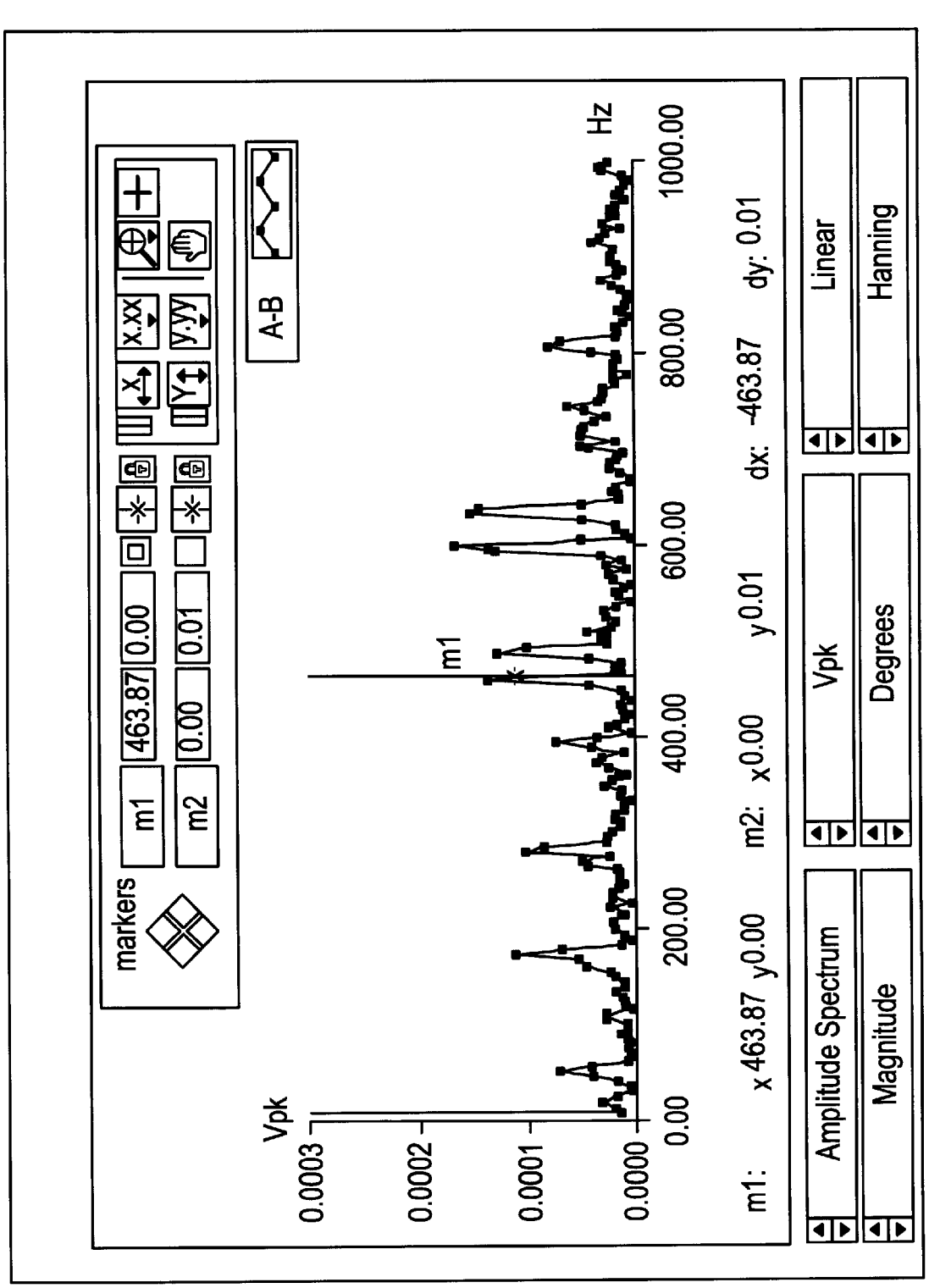
FIG. 4 is a graph similar to FIG. 2 for a second test of damaged tissue.
Figure 5:
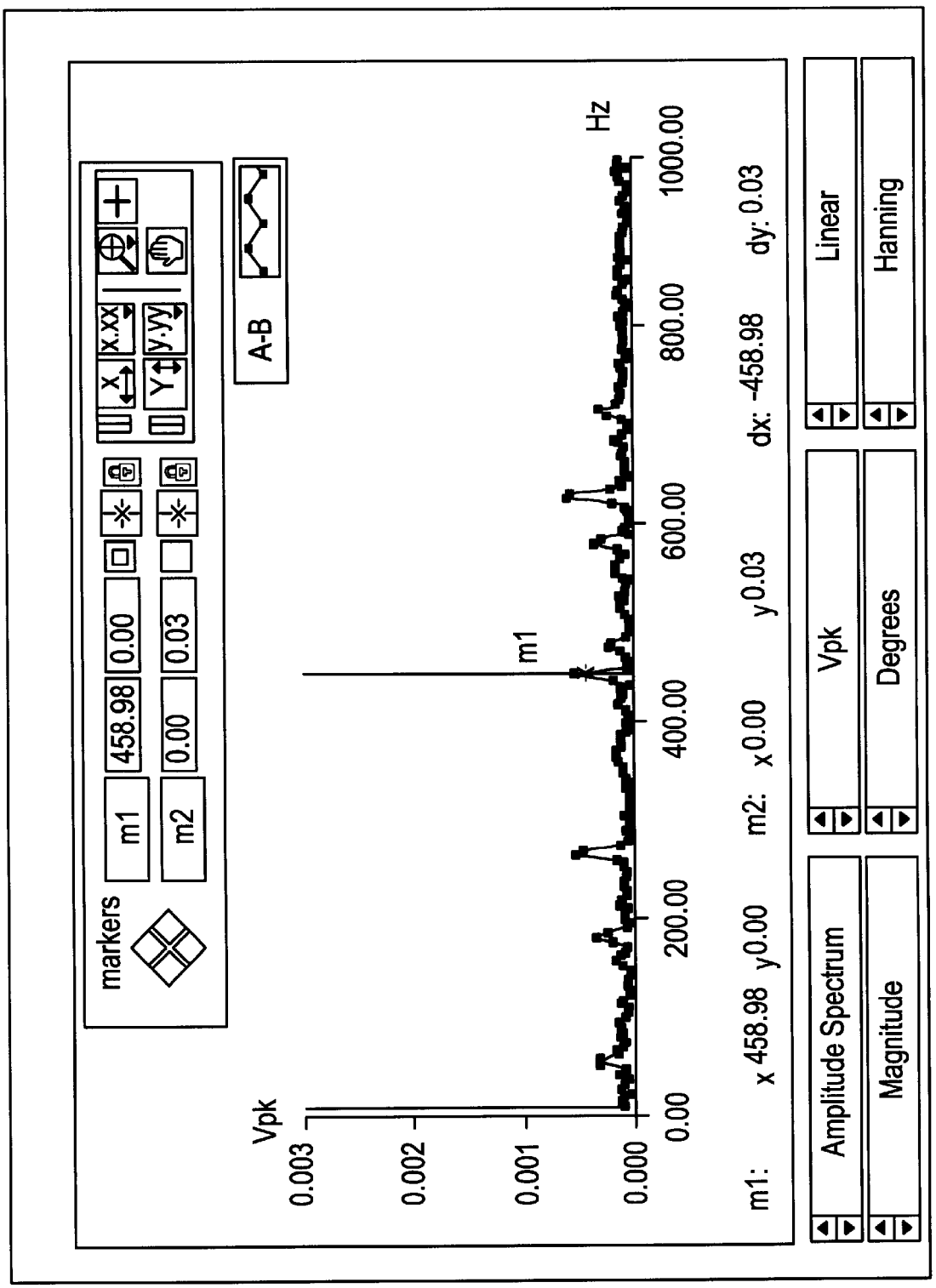
FIG. 5 is a graph similar to FIG. 4 with nerve response inhibited.
Figure 6:
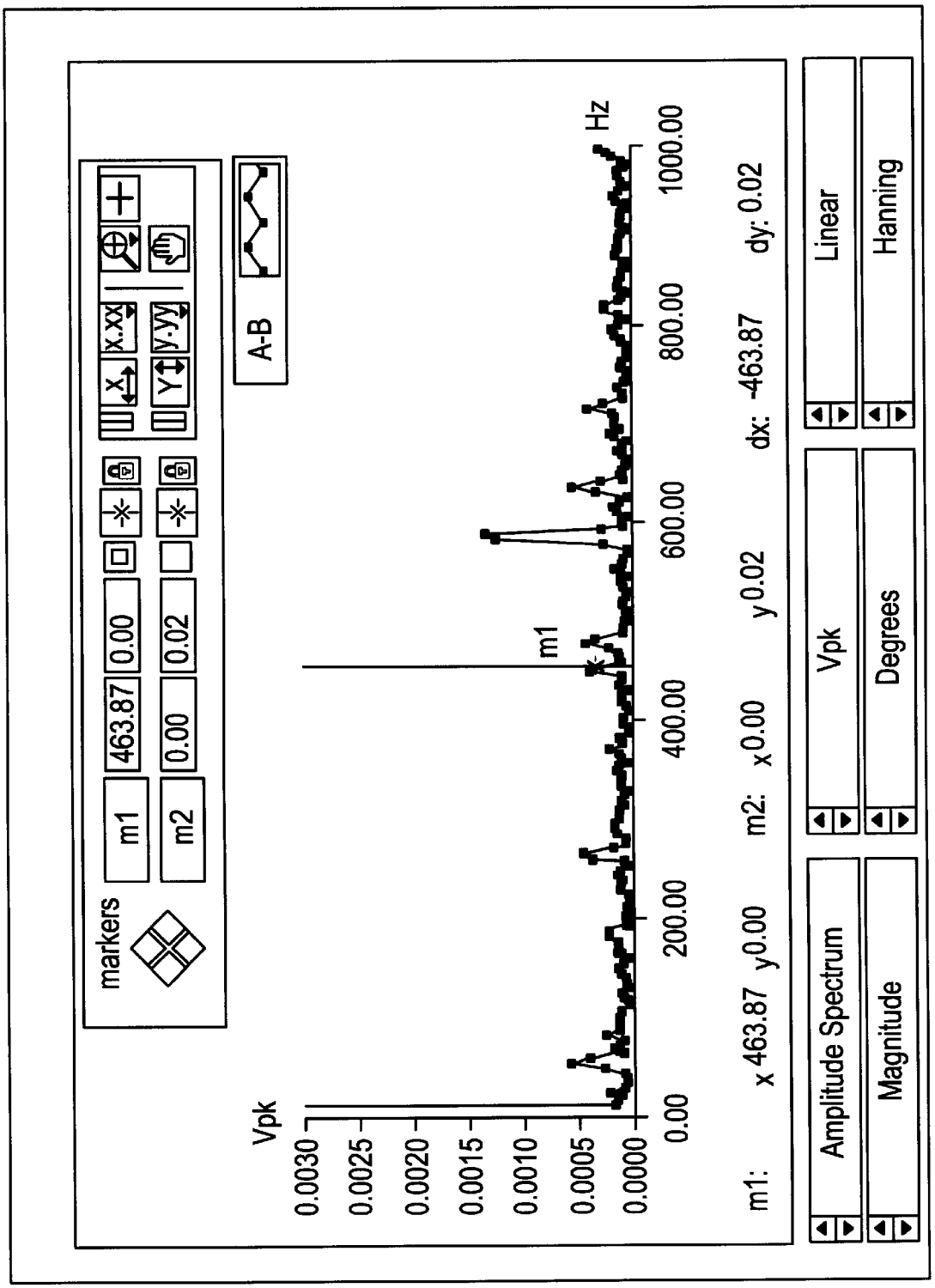
FIG. 6 is a graph similar to FIG. 4 after treatment of the tissue.

In a second test using a different patient, sensor 26 was placed over a barrier of an injured sciatic nerve and sensor 26 was placed over normal uninjured tissue. Acoustic energy at a frequency of 463 hz was emitted from speaker 25 and the results of FIG. 4 were obtained. The data of FIG. 4 exhibits a plurality of spikes at frequencies above 463 hz. Subsequently, without moving sensors 26 and 27 or otherwise changing the test variables, the nerve response was inhibited manually. Particularly, the anchor point of the injured tissue was manually held in position. The results of FIG. 5 were obtained with the nerve response inhibited. Next, and again without moving sensors 26 and 27 or otherwise changing the test variables, the barrier was treated using ACCESS THERAPY™, a procedure described in U.S. provisional application Ser. Nos. 60/052,490 and 60/092,797, the disclosures of which are incorporated herein by reference. Data was collected and processed after treatment and the results are illustrated in FIG. 6. The data of both FIGS. 5 and 6 show attenuated spikes as compared to the data of FIG. 4.

Figure 7:
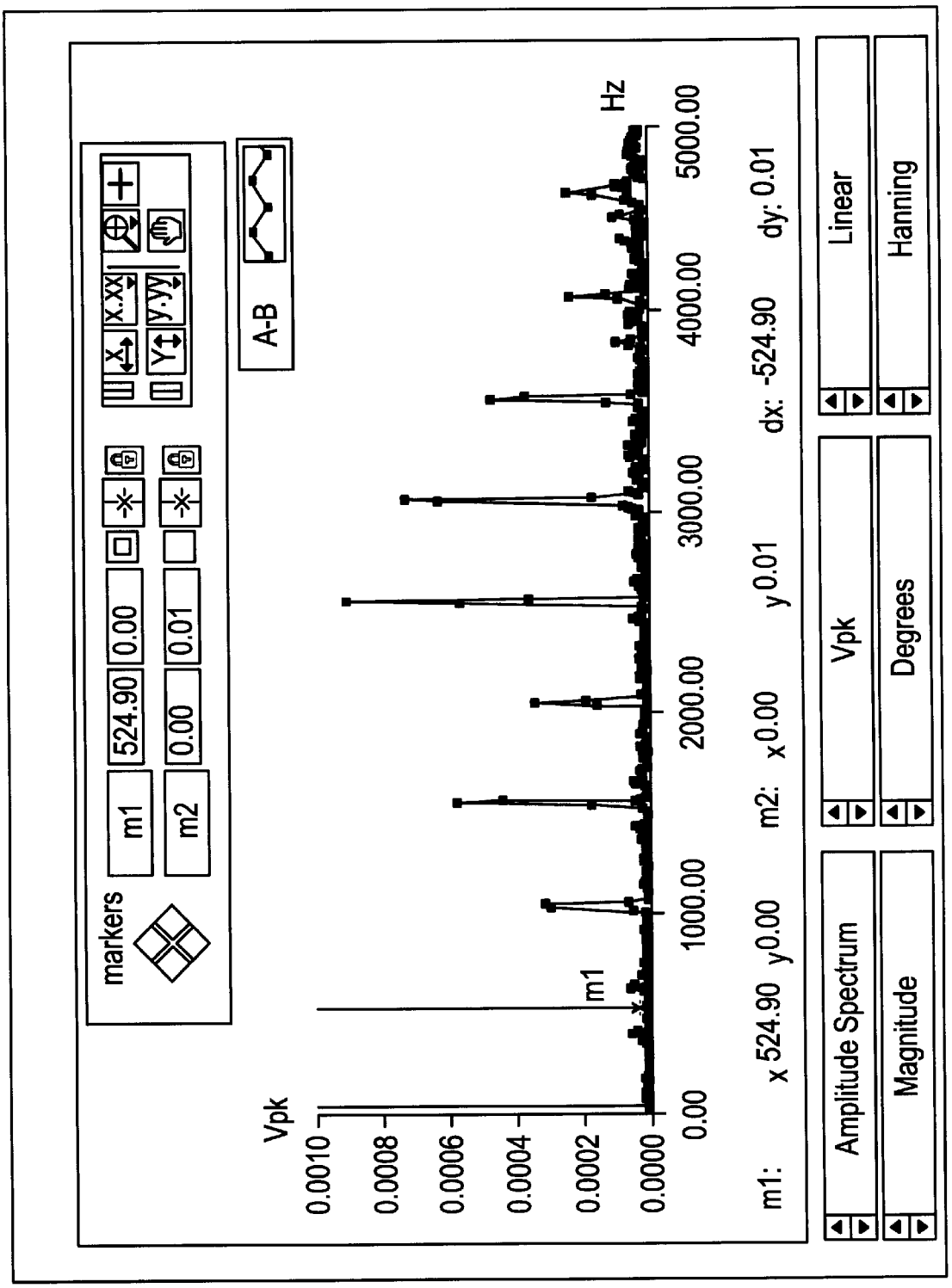
FIG. 7 is a graph similar to FIG. 2 for a third test of damaged tissue.
Figure 8:
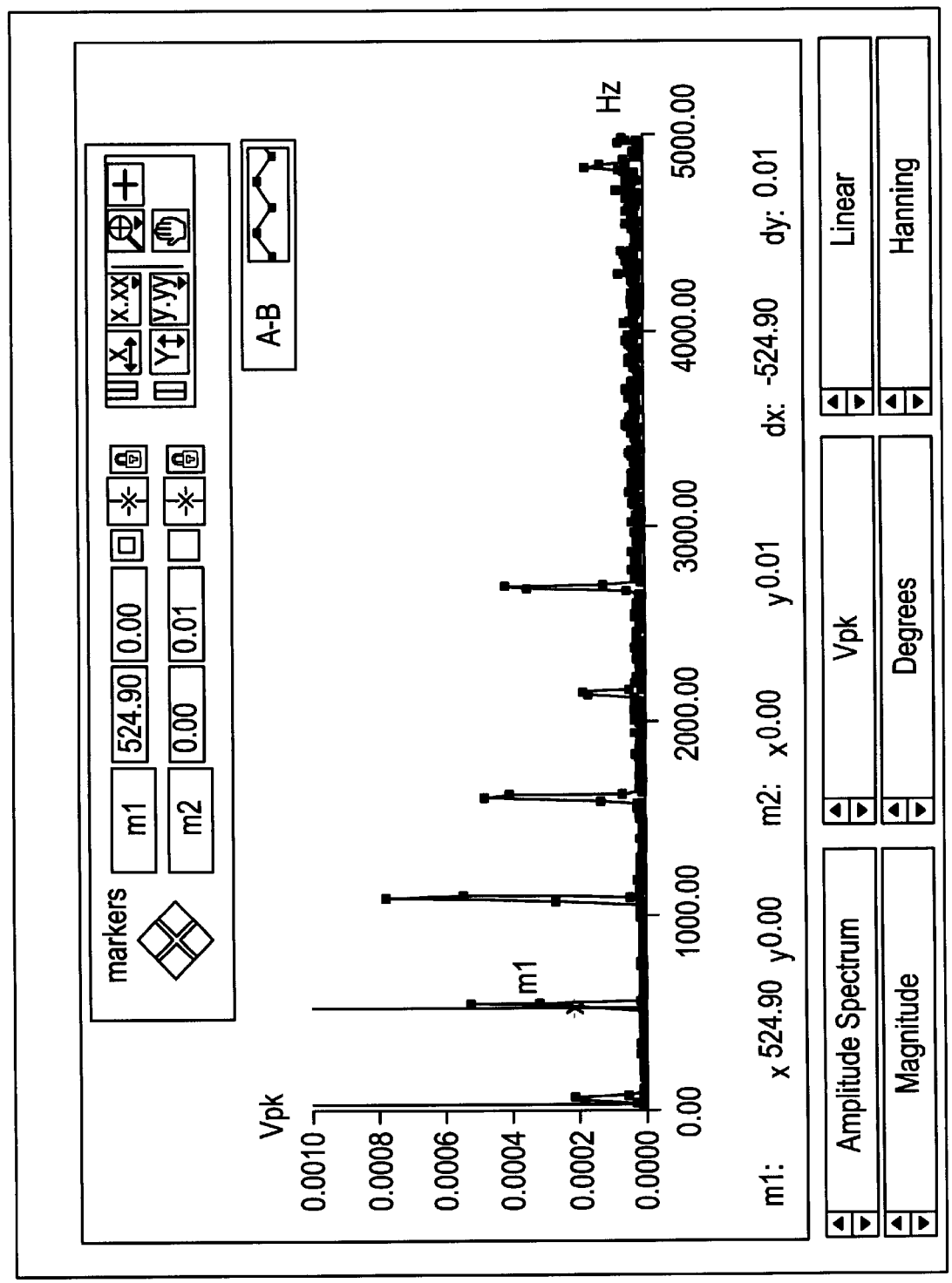
FIG. 8 is a graph similar to FIG. 7 with the nerve inhibited.

In a third test, sensor 26 was placed over a barrier of a trigeminal nerve on a third subject and sensor 27 was placed over an adjacent area of normal tissue. Acoustic energy at a frequency of 524 hz was emitted from speaker 25. FIG. 7 illustrates the results of the third test. Once again, there are observable spikes at frequencies above the driving frequency. The strain was then temporarily alleviated using manual pressure and traction techniques on the anchor and the results are illustrated in FIG. 8. Again, it can be seen that the spikes are attenuated.

The signal from sensor 27 was subtracted from the signal from sensor 26 after scaling and phase shifting in such a way as to minimize the difference between the two signals at the fundamental driving frequency, i.e. the frequency of acoustic energy emitted from speaker to obtain a difference signal. This had the effect of removing the signal due to direct transmission of the fundamental frequency of the excitation signal to sensors 26 and 27. This processing also corrected for the effects of the finite velocity of sound and the differences in amplitude of the two sensors. The difference signal is then Fourier transformed to produce a power spectrum, i.e., a transformed signal showing the various higher and lower frequency modes excited in the tissue. Applicant has found that the transformed signal of injured tissue has significantly higher harmonic content than normal tissue. For example, a strong response is often noted at the first harmonic of the driving frequency of the excitation signal. When the strain is temporarily alleviated using manual pressure and traction techniques on the anchor location, or the barrier site is treated, the harmonic content is significantly attenuated.

The results of the tests discussed above indicate specific quantifiable responses of damaged or stressed soft tissue to acoustical stimulation as compared to normal tissue. Accordingly, the acoustic response principles discussed above can be used to facilitate location of damaged soft tissue and treatment points for therapy, such as the ACCESS THERAPY™ procedure.

Figure 9:
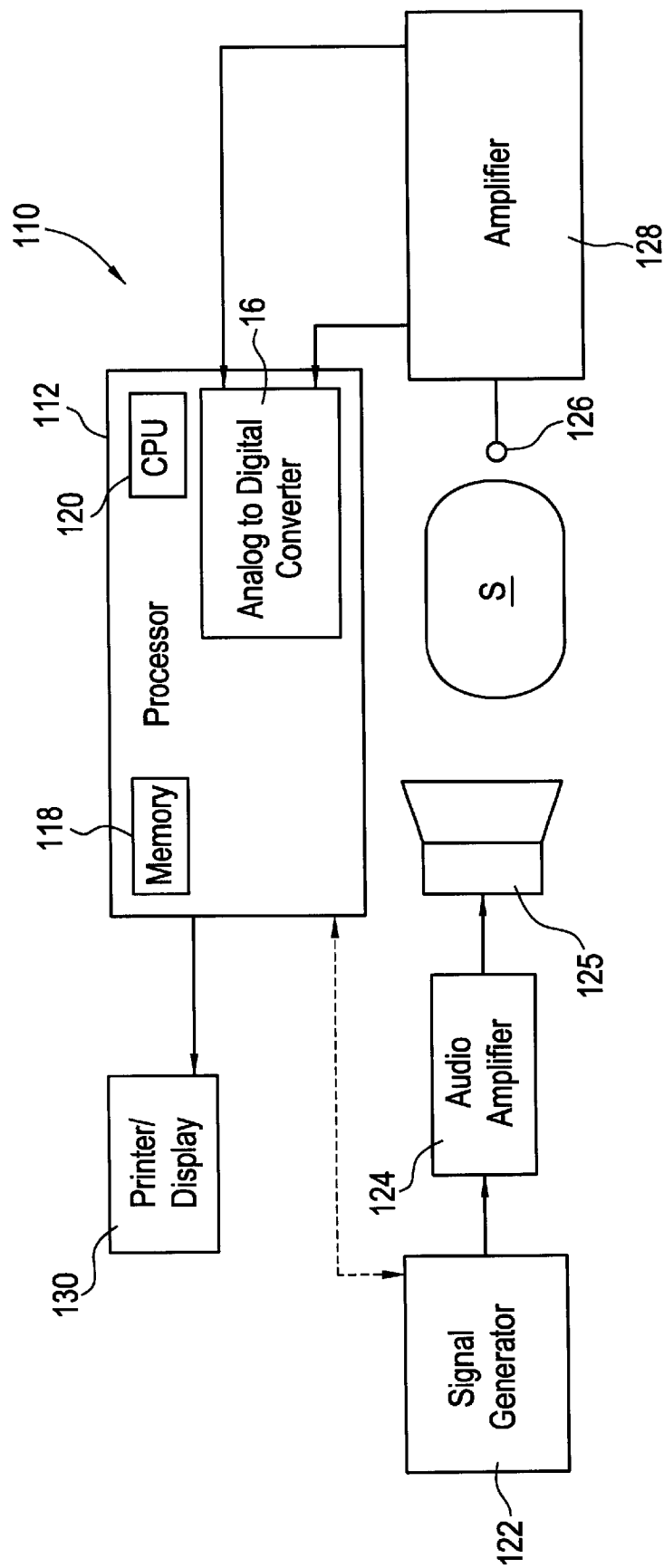
FIG. 9 is a diagnostic apparatus in accordance with the preferred embodiment of the invention.

A preferred embodiment of diagnostic apparatus 100 is illustrated in FIG. 9. Diagnostic apparatus 110 includes processor 112 as an analyzer. In the preferred embodiment processor 112 is a microprocessor based digital device, such as a personal computer. However, any type of analyzer can be used, such as an analog signal processor, or the like. Processor 112 includes analog to digital converter A/D 116. Of course, if processor 112 is analog, A/D 116 can be omitted and replaced by appropriate analog signal interfaces. Processor 112 of the preferred embodiment also has memory device 118, which can include one or more of a random access memory (RAM), a magnetic disk memory device, an optical memory device, or the like, for storing instructions of a control program. Processor 112 also has central processing unit (CPU) 120 for executing the instructions of the control program. Display 130 is coupled to processor 112 to display test results, variables, and the like.

Signal generator 122 is configured to generate an electrical signal of predetermined frequency as described below. The operator can adjust the frequency of the electrical signal or select a progression of frequencies to be generated by signal generator 122 in a known manner. Amplifier 124 receives the electrical signal from signal generator 122 to drive speaker 125 serving as an audio source. The audio source can be any transducer capable of producing an acoustic vibrational signal in response to electrical impulses or other signals, such as a cone speaker, a planar driver speaker, or a piezoelectric device. Also, the signal provided to the audio source can be of any appropriate type. Signal generator 120, amplifier 124, and speaker 1125 constitute an acoustic transmitter in the preferred embodiment. However, the acoustic transmitter can be any device for transmitting acoustic energy, such as a tuning fork, a tone generator, or the like. Preferably, the audio source is highly directional to be capable of isolating particular soft tissue areas.

Audio sensor 126 is coupled to A/D 116 of processor 112 through amplifier 128. Audio sensor 126 and amplifier 128 constitute an acoustic receiver of the preferred embodiment. However, the acoustic receiver can be any device for receiving acoustic energy and distinguishing characteristics thereof, such as a selective resonator, the operator's ear, or the like. Sensor 26 can be a microphone, a stylus, a piezoelectric vibration sensor, an optical motion sensor, an accelerometer, or any other transducer capable of directly or indirectly sensing acoustic energy or motion and outputting a signal related thereto. Sensor 126 can be a contact sensor or a non-contact sensor. Processor 112 can include the necessary processing circuitry or software to eliminate background noise, such as 60 Hz hum, to eliminate any undesired phase or amplitude of the received signal, or to otherwise, linearize, manipulate, transition or enhance the signals received from multi-channel amplifier 128. For example, if a microphone or any other non contact sensor is used as audio sensor 126, it may be necessary to filter out the phase of the audio signal generated by speaker 125 to avoid errors due to direct coupling between speaker 125 and audio sensor 126. Preferably, audio sensor 126 is highly directional to minimize noise and environmental effects. Signal generator 122, amplifier 124 and amplifier 128 can be incorporated in processor 112. For example, a conventional sound card or interface can be used if processor 112 is a personal computer.

As confirmed by the tests discussed above, the acoustic response of damaged or stressed soft tissue has a higher harmonic content than normal tissue when stimulated by acoustic energy. For example, the first and second harmonics have been found to have a much higher amplitude in damaged or stressed tissue. Therefore, if soft tissue S of a patient is placed proximate speaker 125 to be in the path of acoustic energy generated by speaker 125, as illustrated in FIG. 9. Then, soft tissue S will be stimulated when speaker 125 is driven, i.e. emits acoustic energy. For example, stimulation frequencies between 100 and 1000 Hz can be used at 70–90 db. However, different tissue types exhibit different acoustic response characteristics. For example, fluid-filed structures, such as blood vessels, appear to have a maximum response at lower frequencies than do denser and/or smaller structures such as nerves and connective tissue. Sensor 126 is then scanned along soft tissue S by moving sensor 126 relative to soft tissue S. During the scanning, sensor 126 is monitored while the acoustic energy is generated by speaker 125 and the output signal of sensor 126 is recorded in memory 118 and processed. In the preferred embodiment, the output signal of sensor 126 is subjected to Fourier transformation to generate a power spectrum. The transformed signal can then be subjected to threshold evaluation or otherwise processed to determine when the harmonic content, the first and second harmonics in particular, increases significantly. Such an increase is indicative of abnormal tissue. Display 130 can display the transformed signal or merely an indication of abnormal tissue, such as a pilot light, or other indicator.

The electrical signal generated by the signal generator can be of a constant frequency or of a variable frequency over time to find the frequency of maximum response. The frequency can be varied manually in response to operator input or through the control program in a predetermined manner. For example, the frequency can initially be 100 Hz and can be varied in increments of 50 Hz up to 1 kHZ. Applicant has found that most stressed or damaged soft tissue will respond to a frequency within this range. Of course, the range of frequencies, the incremental change, and the rate of change can be varied based on various practical considerations. Also, the amplitude of the acoustic energy signal can be varied as needed.

The audio sensor can be positioned to detect vibration (i.e., responsive acoustic energy) of particular portions of the soft tissue, in response to the acoustic energy generated by the speaker. For example, particular nerves, muscles, ligaments, or the like can be investigated. The audio sensors can be placed over the soft tissue percutaneously or can be directed toward the soft tissue depending on whether the audio sensor is of a type that senses in a contact or non-contact state. Audio sensors employing ultrasound techniques can be used to detect Doppler effects due to resonance of interior organs, blood vessels, or other tissue to permit diagnosis of internal tissue damage or stress. Additional sensors can be used depending on the application and desired resolution of results. Any type of processing can be used to distinguish the response signal of abnormal tissue from that of normal tissue.

As noted above, applicant has found that stressed or damaged soft tissue will respond to a frequency of excitation acoustic energy in a manner that is distinguishable from the response of normalized tissue. Accordingly, stressed and damaged tissue can be distinguished from normalized tissue and accurately located and treated. Also, the effectiveness of treatment can be verified by measuring acoustic response after treatment. These capabilities are especially desirable because often the stressed or damaged tissue is remote from the apparent location of pain indicated by the patient. Testing can provide baselines of normalized tissue to be compared with results of tissue being tested. For example, testing may indicate that a particular area of a patient's hand, in a normalized state, has a particular acoustic profile, transfer function or power spectrum. This can be compared with test results to determine if tissue is stressed or damaged. The control program of the processor can correct any non linearities based on calibration with a known element used in place of the soft tissue.

Living tissue has a complex structure, and not surprisingly, is highly dispersive at acoustic frequencies. To elucidate the difference in acoustic response of the barrier and control sites, the control program of the processor should include instructions for performing processing of data, i.e., response signals, collected by the sensor. In the preferred embodiment, the control program performs a Fourier transform on the sensor output signal. However, any appropriate processing can be accomplished.

Any type of acoustic transmitter and receiver can be used. The analyzer can be configured to accomplish various processing of the sensor signals, such as filtering, transforming, shifting, amplifying, and attenuating. Any type of acoustic sensor can be used. The sensors can be disposed to sense acoustic response of various locations. The invention can be used on any type of soft tissue.

While the invention has been described through a preferred embodiment, various modifications can be made without departing from the scope of the invention as defined by the appended claims.

What is claimed is:

1. A soft tissue diagnostic apparatus for detecting abnormalities in anatomical soft tissue by detecting the response of the soft tissue to acoustic energy, said apparatus comprising:

an acoustic transmitter configured to transmit excitation acoustic energy toward a target area of soft tissue of a subject;

an acoustic receiver configured to receive responsive acoustic energy generated by the soft tissue in response to the excitation acoustic energy transmitted by said acoustic transmitter, said acoustic receiver generating an output signal representative of the response of the soft tissue to the excitation acoustic energy transmitted by said acoustic transmitter;

an analyzer coupled to said acoustic receiver and programmed to detect abnormalities in anatomical soft tissue by detecting the response of the soft tissue to acoustic energy by receiving to the output signal of said acoustic receiver and providing an indication signal of at least one of stress and injury in said soft tissue based on said output signal of said acoustic receiver.

2. A soft tissue diagnostic apparatus for detecting abnormalities in anatomical soft tissue by detecting the response of the soft tissue to acoustic energy, said apparatus comprising:

an acoustic transmitter configured to transmit excitation energy toward a target area of soft tissue of a subject;

an acoustic receiver configured to receive responsive acoustic energy generated by the soft tissue in response to the excitation acoustic energy transmitted by said acoustic transmitter, said acoustic receiver generating an output signal representative of the response of the soft tissue to the excitation acoustic energy transmitted by said acoustic transmitter;

an analyzer coupled to said acoustic receiver to receive the output signal of said acoustic receiver and to provide an indication signal of at least one of stress and injury in said soft tissue based on said output signal of said acoustic wherein said analyzer is coupled to said acoustic receiver and comprises means for eliminating direct effects of the excitation acoustic energy on said acoustic receiver.

3. An apparatus as recited in claim 1, wherein said acoustic transmitter comprises an electrical signal generator operatively coupled to an audio source and said acoustic receiver comprises an audio sensor.

4. An apparatus as recited in claim 3, wherein said analyzer comprises a processor operatively coupled to said audio sensor.

5. An apparatus as recited in claim 4, wherein said processor comprises means for transforming the difference signal into a power spectrum.

6. An apparatus as recited in claim 5, wherein said processor comprises means for performing a Fourier transform on an output signal of said sensor.

7. An apparatus as recited in claim 1, further comprising means for displaying the indication signal.

8. A method of detecting abnormalities in anatomical soft tissue by detecting the response of the soft tissue to acoustic energy, said method comprising the steps of:

transmitting excitation acoustic energy toward a target area of soft tissue of a subject;

receiving responsive acoustic energy generated by the soft tissue in response to the excitation acoustic energy with a sensor;

moving the device relative to the soft tissue;

generating an output signal representative of the responsive acoustic energy; and analyzing the output signal to provide an indication signal of at least one of stress and injury in the soft tissue.

9. A method as recited in claim 8, wherein said transmitting step comprises transmitting the excitation acoustic energy at a variable frequency to determine a maximum response frequency of the soft tissue and subsequently transmitting the excitation acoustic energy at the maximum response frequency.

* * * * *